United States Patent [19]
Takayama et al.

[11] Patent Number: 4,893,614
[45] Date of Patent: Jan. 16, 1990

[54] APPARATUS FOR DISINTEGRATING A CALCULUS BY AN UNDERWATER SHOCK WAVE FROM OUTSIDE THE HUMAN BODY

[75] Inventors: Kazuyoshi Takayama; Masaaki Kuwahara, both of Miyagi; Shuzo Kimura, Chiba, all of Japan

[73] Assignee: Yachiyoda Sangyo Co. Ltd., Tokyo, Japan

[21] Appl. No.: 188,671

[22] Filed: Apr. 29, 1988

Related U.S. Application Data

[63] Continuation of Ser. No. 878,236, Jun. 25, 1986, abandoned.

[30] Foreign Application Priority Data

Jun. 26, 1985 [JP] Japan .................................. 60-137997

[51] Int. Cl.$^4$ ............................................. A61B 17/22
[52] U.S. Cl. .................................... 128/24 A; 128/328
[58] Field of Search ................................ 128/328, 24 A

[56] References Cited

U.S. PATENT DOCUMENTS

| | | | |
|---|---|---|---|
| 3,942,531 | 3/1976 | Hoff et al. | 128/328 |
| 4,196,736 | 4/1980 | Watanabe . | |
| 4,630,607 | 12/1986 | Duinker et al. | 128/328 |
| 4,696,299 | 9/1987 | Shene et al. | 128/328 |

FOREIGN PATENT DOCUMENTS

| | | | |
|---|---|---|---|
| 90138 | 10/1983 | European Pat. Off. | 128/328 |
| 1621366 | 5/1971 | Fed. Rep. of Germany . | |
| 2538960 | 4/1977 | Fed. Rep. of Germany | 128/328 |
| 2913251 | 10/1980 | Fed. Rep. of Germany | 128/328 |
| 3119295 | 12/1982 | Fed. Rep. of Germany | 128/328 |
| 3220751 | 12/1983 | Fed. Rep. of Germany . | |
| 3328039 | 2/1985 | Fed. Rep. of Germany . | |

OTHER PUBLICATIONS

Dornier Medizintechnik GmgH, Gemering 1 (pamphlet).

Primary Examiner—Michael H. Thaler
Attorney, Agent, or Firm—Sandler & Greenblum

[57] ABSTRACT

An apparatus for disintegrating a calculus in the human body by an underwater shock wave produced outside the human body. The apparatus includes a shock wave generation chamber having an inner surface in the shape of a part of a pseudo-ellipsoid of revolution having an opening therein. Also provided is a shock wave generation source positioned at the first focus of the pseudo-ellipsoid of revolution. In addition, a flexible container housing a liquid is attached to the shock wave generation chamber so that the liquid from the flexible container fills up the shock wave generation chamber. The flexible container containing the liquid is brought into contact with the human body, and the shock wave generation chamber is displaced so as to deform the flexible container, until the calculus in the human body is positioned at the second focus of the pseudo-ellipsoid of revolution. As a result of this positioning of the calculus of the human body at the second focus of the pseudo-ellipsoid of revolution, when a shock wave is generated at the first focus, a sufficiently high pressure can be generated at the second focus so as to disintegrate the calculus.

33 Claims, 2 Drawing Sheets

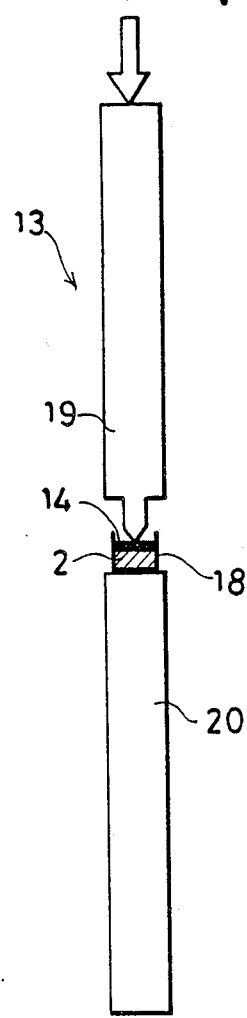
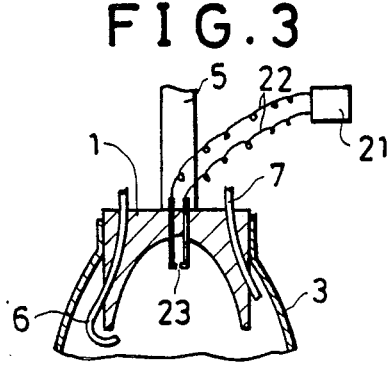
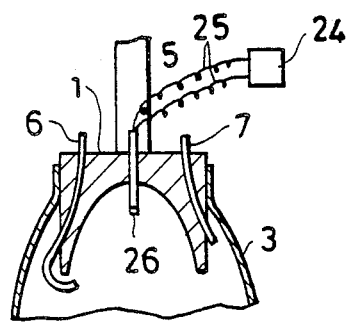
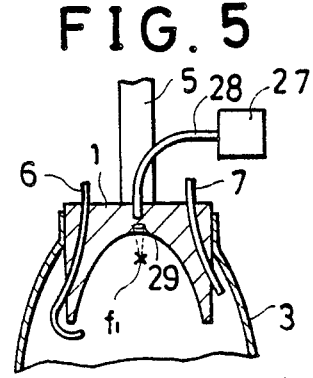

4,893,614

APPARATUS FOR DISINTEGRATING A CALCULUS BY AN UNDERWATER SHOCK WAVE FROM OUTSIDE THE HUMAN BODY

This application is a continuation of application Ser. No. 878,236, filed June 25, 1986, abandoned.

BACKGROUND OF THE INVENTION

1. Field of the Invention

The invention relates to an apparatus for disintegrating a calculus in a human body.

2. Description of Pertinent Information

Devices for disintegrating a calculus in a human body comprise a shock wave generation chamber having an inner surface formed in the shape of a pseudo-ellipsoid of revolution. The pseudo-ellipsoid of revolution has two foci. As a result, a shock generated at one focus will be concentrated at the other focus.

In order to use the device, a patient is immersed in a tank filled with liquid. The tank is brought into contact with an open portion of the shock wave generation chamber so that the chamber is filled with the liquid. A shock wave is generated, for example, by a spark discharge, at the first focus of the pseudo-ellipsoid of revolution. Before this spark is generated, the patient is so positioned so that the calculus in the patient is positioned at the second focus of the pseudo-ellipsoid of revolution. As a result, when the shock wave is generated, the calculus is broken by the shock wave.

This conventional device has several advantages. First, the calculus can be broken without any physical or mental pain being produced in the patient. Second, a long stay for treatment in the hospital is not required, inasmuch as this treatment takes a relatively short amount of time. However, because a liquid filled tank for immersion of the patient is required, the apparatus must be large in size and cannot be transported easily. Additionally, this apparatus is inconvenient because if a patient has a skin eczema, an external injury, or similar problem, the patient cannot be immersed in the liquid filled tank for treatment until the patient has recovered.

Thus, there is a need for an apparatus that disintegrates a calculus in the human body that is small, can be easily transported, and does not require immersion of the patient in a liquid.

SUMMARY OF THE INVENTION

It is an object of the present invention to provide an apparatus for disintegrating a calculus in a patient which overcomes the disadvantages of the prior art.

It is still another object of the present invention to provide an apparatus that disintegrates a calculus in the human body that is small, can be easily transported, and does not require the immersion of the patient in a liquid.

The invention which achieves these objectives relates to an apparatus for disintegrating a calculus in the human body by an underwater shock wave from outside the human body. The apparatus comprises a shock wave generation chamber, a shock wave generation source in the chamber for generating a shock wave, and a flexible container connected to the shock wave generation chamber, and adapted to receive a liquid. The shock wave generation chamber has an interior and an opening therein, which receives liquid from the flexible container. Further, the shock wave generation chamber is adapted to be positioned so that the interior of the chamber is filled through its opening with the liquid in the container when the flexible container is filled with the liquid. In one embodiment the invention relates to this apparatus in combination with the liquid, which can be water. The shock wave generation chamber has an inner surface formed in the shape of a part of a pseudo-ellipsoid of revolution having first and second foci. The shock wave generation source is positioned substantially at the first focus of the pseudo-ellipsoid of revolution. As a result, when a calculus in the human body is positioned at the second focus of the pseudo-ellipsoid of revolution, this calculus is disintegrated in response to the generation of a sufficiently strong the shock wave at the first focus.

In one embodiment the shock wave generation means comprises means for producing a shock wave of sufficient strength at the first focus so as to disintegrate a calculus comprising a stone of calcium oxalate as large as 5 millimeters in diameter at the second focus. The shock wave generation source can comprise a microexplosive comprising 5 milligrams of lead azide. In addition, in one embodiment the shock wave generation source comprises a material selected from the group consisting of: lead azide, silver azide, tricinate, and diazo dinitro phenol.

In one embodiment, the human body is placed on a bed. In this embodiment the apparatus comprises means for displacing at least one of the bed and the shock wave generation chamber so that the flexible container contacts the human body and so that the calculus of the human body is substantially positioned at the second focus of the pseudo-ellipsoid of revolution.

In one embodiment the shock wave generation source comprises a microexplosive. In an alternative embodiment, the shock wave generation source comprises a spark gap generating apparatus comprising a high voltage electric source, and two spaced apart plates forming a gap therebetween and connected to the source of electricity. The source of electricity produces a spark in the gap at the first focus. In still another embodiment, the shock wave generation source comprises a supersonic wave generation element and an electric source connected to the element. In still another alternative embodiment, the shock wave generation source comprises means for producing a laser beam, an optical fiber means, and a focusing lens. The fiber optical means transmits the laser beam from the laser means to the lens, and the lens is so positioned so as to focus the laser beam outputted from the fiber optic means at the first focus of the pseudo-ellipsoid of revolution in the shock wave generation chamber.

In the embodiment in which the shock wave generation source comprises a microexplosive, a trigger means is provided for the microexplosive. The trigger comprises an initiating explosive which is in contact with the microexplosive, an optical fiber means which is in contact at one end with the initiating explosive, and a laser beam generation means connected to the other end of the optical fiber means.

Alternatively, in the embodiment in which the shock wave generation source comprises a microexplosive, the triggering means can comprise an initiating explosive in contact with the microexplosive, an electrical heater embedded in the microexplosive, an electrical wire which is connected at one end to the heater, and a switch box having a dry battery electric source connected to the other end of the electric wire.

In still another embodiment in which the shock wave generation source comprises a microexplosive, the triggering means for the microexplosive comprises an initiating explosive adhered to the microexplosive. In this embodiment the microexplosive is placed in an easily breakable casing. Also provided is a triggering rod, which has a rear end and a tapered forward end which is in contact with the initiating explosive. Also provided is a receiving rod for supporting the other side of the casing between the initiating explosive and the triggering rod, and striking means for providing a blow or striking the rear end of the triggering rod at a high speed. The striking means provides a blow at a sufficiently high speed to trigger the initiating explosive and, therefore the microexplosive.

In one embodiment the invention relates to the apparatus noted above in combination with a liquid. This liquid, for example may be water. Further, the flexible container can be composed of a film of synthetic rubber, or synthetic resin.

In still another embodiment, the container comprises an open mouth portion mounted at the periphery of the shock wave generation chamber.

In still another embodiment, the apparatus further comprises a liquid or water flow jet positioned in the container, for removing bubbles from the inner surface of the chamber. One end of the jet is directed toward the shock wave generation chamber so that a jet of liquid such as water flows along an inner surface of the shock wave generation chamber for removing or sweeping bubbles, such as air bubbles, which adhere to the inner surface of the shock wave generation chamber. The other end of the jet is attached to a tank filled with liquid. Also a pipe may be provided for filling the container with liquid or for discharging the liquid from the container. The microexplosive can comprise lead azide, silver azide, tricinate, diazo dinitro phenol (DDNP) or similar substance. In one embodiment, 10 mgs. of lead azide are used, which generates a shock wave of 3,000 times atmospheric pressure at the second focus. In an alternative embodiment, 5 mgs. of lead azide is used, which generates a pressure at the second focus 2,500 times atmospheric pressure, thereby disintegrating a calculus as large as 5 millimeters in diameter with one explosion.

In still another embodiment the invention relates to an apparatus for disintegrating a calculus in a human body comprising a container adapted to receive and hold a liquid, a shock wave generation source positioned at least partially in the container, and means for permitting relative displacement between the source and the container. The container is flexible so as to permit the relative displacement of the source and the container. As a result, the container comprises the means for permitting relative displacement between the source and the container. In addition, the displacement means comprises means for permitting displacement of the source while the container is in contact with the human body.

The apparatus further comprising a shock wave generation chamber in communication with the container so that when the container is filled with liquid the shock wave generation chamber is filled with liquid. The shock wave generation chamber has an inner surface in the shape of a pseudo-ellipsoid of revolution having first and second foci. The source is positioned substantially at the first focus, whereby the position of the second focus can be changed sufficiently to substantially coincide with the location of the calculus in response to the relative displacement of the source and the container while the container is in contact with the human body.

The container comprises an open mouth portion fastened to the chamber so that the chamber-container combination holds a liquid when the container-chamber combination is filled with a liquid. In addition, the source comprises means for generating a shock wave of sufficient strength at the first focus so as to disintegrate the calculus at the second focus. Also, the source comprises means for generating a shock wave at the first focus of sufficient strength to disintegrate a calculus at the second focus comprising a stone of calcium oxalate as large as 5 millimeters.

In order to use the apparatus a human body containing the calculus is placed on a bed, and the container is brought into contact with the human body. Then, either the bed or the chamber is displaced until the calculus is positioned at the second focus. As a result, the apparatus must further comprise means for displacing at least one of the bed and the chamber so as to position the calculus at the second focus.

In one embodiment the source comprises a microexplosive. In an alternative embodiment the source comprises a spark gap generating apparatus comprising a source of electricity and two spaced apart plates connected to the electricity source. The source of electricity produces a spark in the gap at the first focus. In still another embodiment the source comprises a supersonic wave generation element. In still another alternative embodiment the source comprises means for producing a laser beam, an optical fiber means, and a focusing lens. One end of the optical fiber means is connected to the laser means and the other end of the optical fiber means is directed toward the lens. The lens is so positioned to focus the laser beam outputted from the optical fiber means at substantially the second focus.

The apparatus further comprising a liquid jet directed toward the inner surface of the chamber for directing a flow of liquid at the inner surface of the chamber to remove bubbles adhering to the inner surface of the chamber.

In addition, the apparatus further comprising a pipe passing through the chamber so that one end of the pipe is positioned in the container. The other end of the pipe is connected to a source of liquid. As a result, the pipe comprises means for filling the container with the liquid.

Alternatively, the pipe is connected to means for discharging liquid from the container through the pipe. The pipe again passes through the chamber so that one end of the pipe is positioned in the container, and the other end of the pipe is connected to the discharging means.

BRIEF DESCRIPTION OF THE DRAWINGS

The invention will be better understood with reference to the detailed description which follows, and the attached drawings in which:

FIG. 2(c) illustrates a cross-sectional view of another alternative embodiment of the trigger apparatus of the present invention;

FIGS. 3-5 illustrate cross-sectional views of alternative embodiments of the present invention.

DETAILED DESCRIPTION OF PREFERRED EMBODIMENTS

The present invention relates to a calculus disintegrating apparatus. The apparatus comprises a shock wave generation chamber having an inner surface formed in the shape of a part of a pseudo-ellipsoid of revolution, which is filled with a liquid. The pseudo-ellipsoid of revolution forms first and second foci. Also provided is a shock wave generation source for generating a shock wave at the first focus of the pseudo-ellipsoid of revolution, so that a calculus of a human body positioned at the second focus of the pseudo-ellipsoid of revolution is disintegrated by the generated shock wave. In addition, a flexible container containing the liquid is provided, which is attached to the shock wave generation chamber. The shock wave generation chamber is so positioned with respect to the container that the interior of the chamber is filled through an opening therein with the liquid in the container.

This apparatus operates as follows.

The flexible container containing the liquid is brought into contact with a human body. Either the human body or the shock wave generation chamber is displaced, thereby deforming the flexible container, until the calculus in the human body is positioned at the second focus of the pseudo-ellipsoid of revolution. Then a shock wave is generated at the first focus of the pseudo-ellipsoid of revolution in the shock wave generation chamber. The shock wave is transmitted to the human body through the container and a high pressure is generated at the second focus of the pseudo-ellipsoid of revolution, i.e., at the position of the calculus. As a result, the calculus is disintegrated, if a sufficient pressure is generated by the shock wave.

Figure 1:
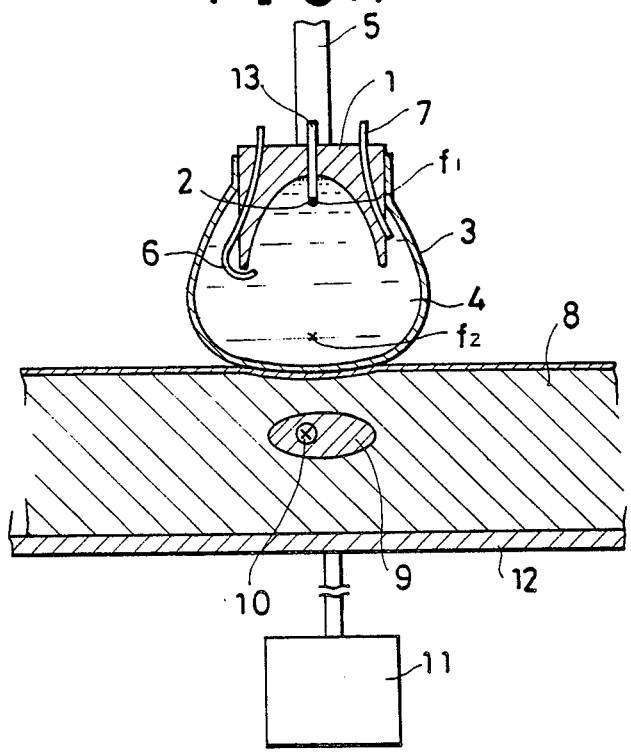
FIG. 1 illustrates a cross-sectional view of one embodiment of the present invention.

FIG. 1 illustrates one embodiment of the present invention. The invention comprises a shock wave generation chamber 1 having an inner surface formed in the shape of a part of a pseudo-ellipsoid of revolution. The apparatus further comprises a microexplosive 2 functioning as a shock wave generation source. Microexplosive 2 explodes in response to the actuation of a trigger mechanism 13 which will be described below. Microexplosive 2 is positioned at a first focus $f_1$ of the pseudo-ellipsoid of revolution in shock wave generation chamber 1. This is accomplished by inserting microexplosive 2 into shock wave generating chamber 1 through an opening therein.

Also provided is a flexible container composed of a film of synthetic rubber, synthetic resin, or similar substance. Container 3 is adapted to receive a liquid 4, such as water. Container 3 has an open mouth portion at its upper end when viewed in FIG. 1. This open mouth portion of container 3 is mounted at the periphery of shock wave generation chamber 1, as is illustrated in FIG. 1. The open mouth portion of container 3 is fastened to the periphery of the shock wave generation chamber 1 by fastening means such as a fastening band, pins, or similar device (not shown) which is applied to the periphery of shock wave generation chamber 1.

Shock wave generation chamber 1 is supported on a supporting rod 5, which is attached to a stationary base (not illustrated). The interior of chamber 1 is filled with liquid 4 through the opening in chamber 1.

The apparatus further comprises a water or liquid flow jet 6 through which a liquid, such as water flows from a source of liquid (not shown). Jet 6 is designed to remove bubbles, such as air bubbles, which may form in chamber 1. One end of jet 6 is directed toward shock wave generation chamber 1 so that a jet of water flows out of jet 6 and flows along an inner surface of chamber 1, thereby removing or sweeping air bubbles which adhere to the inner surface of chamber 1.

Also provided is a pipe 7, one end of which is also positioned in container 3. Pipe 7 is adapted to be connected to either a source of liquid to fill container 3 with that liquid, or, pipe 7 is adapted to be connected to an empty tank and means for discharging the liquid from container 3 into that tank through pipe 7, so that the liquid in container 3 can then be replaced with fresh liquid through pipe 7.

Numeral 8 in FIG. 1 denotes a human body having a calculus 10 at any of the internal organs of the human body, such as at the kidney, the gall bladder, or similar organ. Human body 8 is laid on a bed 12 which comprises means for displacing the bed in any desired direction i.e., along the horizontal X axial and Y axial directions and in the vertical direction. This displacing of the bed in the horizontal and vertical directions is performed and controlled by a control box 11 in order to carry out the calculus disintegrating treatments.

Figures 2A, 2B:
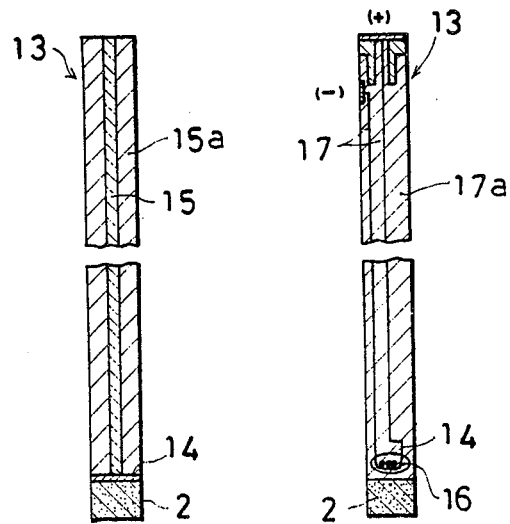
FIG. 2(a) illustrates a cross-sectional view of the trigger mechanism of the present invention.
FIG. 2(b) illustrates a cross-sectional view of an alternative embodiment of the trigger mechanism of the present invention.

Microexplosive 2 comprises a shock wave generation source. Microexplosive 2 is exploded by a trigger means 13, a significant portion of which is shown in FIGS. 2(a), FIG. 2(b) and FIG. 2(c). Each of these figures represent alternative embodiments of trigger means 13.

In one embodiment illustrated in FIG. 2(a) trigger means 13 comprises an initiating explosive 14 which is positioned in contact with microexplosive 2. Trigger 13 also comprises an optical fiber means 15 which passes through a covering tube 15a. One end of optical fiber means 15 is in contact with initiating explosive 14, and the other end of optical fiber means 15 is in contact with a laser generation means (not illustrated), such as a ruby laser with a Q switch, a YAG laser with a Q switch, or similar device. When the laser is turned on, the energy from the laser is transmitted through the optical fiber means 15 and explodes initiating explosive 14, which in turn explodes microexplosive 2.

FIG. 2(b) shows an alternative embodiment of trigger means 13. In this embodiment, initiating explosive 14 is again positioned in contact with microexplosive 2. However, in this embodiment an electrical heater 16 is embedded in the initiating explosive 14. Also provided is electrical wire 17. One end of electrical wire 17 is connected to heater 16. Wire 17 is covered by insulation material 17a. The other end of electric wire 17 is connected to a dry battery electric source in a switch box (not illustrated) providing 6-9 volts. When the switch in the switch box is closed, electricity from the battery passes through wire 17 so as to heat electrical heater 16, thereby exploding initiating explosive 14, which in turn, causes microexplosive 2 to explode and generate a shock wave.

Still another embodiment of the triggering means 13 as illustrated in FIG. 2(c).

In FIG. 2(c) an initiating explosive 14 is positioned in contact with and adheres to microexplosive 2. Microexplosive 2 and explosive 14 are placed in a easily breakable casing 18. Also provided is a triggering rod 19 which has a rear end and a forward tapered end which is in contact with initiating explosive 14. Also provided is a receiving rod 20 for supporting casing 18. As a result, casing 18 is positioned between trigger rod 19 and receiving rod 20. Finally, a striking means (not illustrated) is provided which produces a blow at a sufficiently high speed to the rear end of trigger rod 19 so as to cause the forward tapered end of trigger 19 to break casing 18 and be introduced into the initiating explosive 14 to explode initiating explosive 14, thereby triggering the explosion of microexplosive 2 by the mutual friction of crystals of initiating explosive 14.

When trigger means 13 illustrated in FIG. 2(c) is used, trigger rod 19 and receiving rod 20 are inserted and positioned horizontally in shock wave generation chamber 1, while microexplosive 2 and initiating explosive 14 are positioned between rods 19 and 20.

Microexplosive 2 may be made from a variety of explosives such as lead azide, silver azide, tricinate, diazo dinitro phenol (DDNP), or similar substance.

The energy generated can be varied according to the following formulas:

| | | | |
|---|---|---|---|
| 1. | Lead azide | 1.5 joule/mg | Specific gravity 2 g/cm$^3$ |
| 2. | Tricinate | 1.8 joule/mg | Specific gravity 2 g/cm$^3$ |
| 3. | DDNP | 3.3 joule/mg | Specific gravity 1.58 g/cm$^3$ |
| 4. | Silver azide | 1.5 joule/mg | Specific gravity 1.8 g/cm$^3$ |

The pressure generated at the second focus when explosive 2 is changed in weight is described below, and varies in proportion to the cubic root of the weight of the explosive.

| | | |
|---|---|---|
| Lead azide | 10 mg. | about 3000 atmospheric pressure |
| Lead azide | 5 mg. | about 2500 atmospheric pressure |

Accordingly, by varying the kind and the amount of the explosives, the optimum energy amount, that is the pressure at the second focus, can be predetermined.

Thus, in the foregoing embodiment, microexplosive 2, of a proper amount is positioned at the first focus of the shock wave generation chamber 1, and human body 8 is laid on bed 12 and is brought into contact through grease, or similar substance, with the bottom portion of flexible container 3.

Next, control box 11 of the bed is operated so as to move the bed in the X axial and Y axial horizontal direction, and in the upper and lower directions so as to position the calculus 10 of human body 8 at substantially second focus position $f_2$. In accordance with the experiments conducted by Applicants, it has been confirmed that when microexplosive 2 comprises 5 mgs. of lead azide and this lead azide is exploded at the first focus, a calculus at the second focus comprising a stone of calcium oxalate as large as 5 mm. in diameter can be disintegrated by one explosion of microexplosion 2.

In the embodiments discussed above, bed 12 comprises means for displacing bed 12. However, it is within the scope of the invention for bed 12 to be fixed and for shock wave generation chamber 1 to be provided with means for moving chamber 1 vertically and horizontally via a movable table (not shown) attached to supporting rod 5 which supports chamber 1.

In addition, as noted above, in the above embodiments microexplosive 2 is used for a shock wave generation source. However, it is within the scope of the invention, as illustrated in FIG. 3, for the shock wave generation source to be a spark gap generator. In this embodiment, an electrical spark is generated to bridge the gap 23 between two plates. Each plate is connected to an electric wire 22, and each wire 22 is connected to a high voltage electric source 21.

In an alternative embodiment, shock wave generation source 2, as illustrated in FIG. 4, can comprise a supersonic shock wave generation element 26. Element 26 is connected, through an electric wire 25 to an electric source 24.

Alternatively, the shock wave generation mechanism can comprise the laser 27, such as a YAG laser with a Q switch, or similar device, an optical fiber means 28, and a focusing lens 29. One end of optical fiber means 28 is connected to the laser, and the other end faces lens 29. As a result, light from laser 27 passes through optical fiber means 28 and is focused by lens 29 on the first focus $f_1$ of the pseudo-ellipsoid of revolution of shock wave generation chamber 1.

As a result of the novel calculus disintegration apparatus discussed above, a calculus in the human body can be easily disintegrated without the necessity of immersing the patient in a tank filled with liquid. Thus, even a patient having a disease which prevents the patient from being immersed in liquid can be treated because immersion in a tank filled with liquid is not required. Further, because there is no need for immersion of the patient in a tank filled with liquid, the apparatus for disintegrating the calculus can be made small and can be easy to transport.

Although the invention has been described with respect to particular means, methods and embodiments, the invention is not limited thereto, but extends to all equivalents within the scope of the claims.

What is claimed is:

1. An apparatus for disintegrating a calculus in a human body by generating an under-water shock wave from outside the human body, said apparatus comprising:
   (a) a shock wave generation chamber having an interior surface and an opening, said shock wave generation chamber further comprising a substantially solid exterior side surface that surrounds said interior surface and said opening;
   (b) a shock wave generation source for generating a shock wave in said shock wave generation chamber; and
   (c) an entirely flexible container which is adapted to receive a liquid, said shock wave generation chamber being positioned so that the interior of said shock wave generation chamber is filled through said opening with liquid from said flexible container when said flexible container is filled with said liquid, said flexible container having an open mouth portion which is positioned about the exterior side of said shock wave generation chamber, wherein said shock wave generation chamber has a solely pseudo-elliptical interior surface said flexible container further having an interior which is in fluidic communication with the pseudo-elliptical interior surface, and means for retaining side open mouth portion of said flexible container about the exterior said surface of said shock wave generation chamber, wherein most of the exterior side surface of said shock wave generation chamber is in fluidic communication with the interior of the flexible container.

2. The apparatus defined by claim 1, in combination with said liquid.

3. The apparatus defined by claim 2, wherein said liquid is water.

4. The apparatus defined by claim 1, wherein said interior surface having the shape of a part of said pseudo-ellipsoid of revolution has first and second foci, said shock wave generation source being positioned substantially at said first focus of said pseudo-ellipsoid of revolution, whereby when said calculus is positioned at said second focus of said pseudo-ellipsoid of revolution, said calculus is disintegrated in response to a sufficiently strong shock wave generated by said shock wave generation source at said first focus.

5. The apparatus defined by claim 4, wherein said shock wave generation source comprises means for producing a shock wave of sufficient strength so as to disintegrate a calculus comprising a stone of calcium oxalate as large as 5 millimeters in diameter.

6. The apparatus defined by claim 5, wherein said shock wave generation source comprises a microexplosive comprising 5 milligrams of lead azide.

7. The apparatus defined by claim 4, wherein said shock wave generation source comprises a material selected from the group consisting of: lead azide, silver azide, tricinate, and diazo dinitro phenol.

8. The apparatus defined by claim 4, wherein said human body is placed on a bed, wherein said apparatus further comprises means for displacing at least one of said bed and said shock wave generation chamber so that said flexible container contacts said human body, and so that said calculus in said human body is positioned substantially at said second focus of said pseudo-ellipsoid of revolution.

9. The apparatus defined by claim 4 wherein said shock wave generation source comprises a microexplosive.

10. The apparatus defined by claim 4, wherein said shock wave generation source comprises a spark gap generating apparatus, wherein said spark gap generating apparatus comprises a source of high voltage electricity, and two spaced apart plates forming a gap therebetween and connected to said source of electricity, wherein said source of electricity produces a spark in said gap at said first focus.

11. The apparatus defined by claim 4, wherein said shock wave generation source comprises a supersonic wave generation element and a source of electricity connected to said element.

12. The apparatus defined by claim 4, wherein said shock wave generation source comprises means for producing a laser beam, an optical fiber means, and a focusing lens, wherein said optical fiber means transmits said laser beam from said laser means to said focusing lens, and wherein said focusing lens is so positioned so as to focus said laser beam outputted from said fiber optical means at said first focus of said pseudo-ellipsoid of revolution in said shock wave generation chamber.

13. The apparatus defined by claim 4, wherein said shock wave generation source comprises a microexplosive, and a trigger means for triggering said microexplosive, wherein said trigger means comprises an initiating explosive, an optical fiber means, and means for generating a laser beam, wherein said initiating explosive is in contact with said microexplosive, wherein one end of said optical fiber means is in contact with said initiating explosive, and wherein the other end of said optical fiber means is connected to said laser generation means.

14. The apparatus defined by claim 4, wherein said shock wave generation source comprises a microexplosive, and means for triggering said microexplosive, wherein said triggering means comprises an initiating explosive, an electrical heater, an electric wire, and a switch box comprising a dry battery electric source, wherein said initiating explosive is in contact with said microexplosive, said electric heater is embedded in said initiating explosive, wherein one end of said wire is connected to said heater, wherein the other end of said electric wire is connected to said dry battery electric source in said switch box.

15. The apparatus defined by claim 4, wherein said shock wave generation source comprises a microexplosive, and means for triggering said microexplosive, wherein said triggering means comprises an initiating explosive, a triggering rod, and a receiving rod, wherein said initiating explosive adheres to said microexplosive, wherein said apparatus further comprises a breakable casing in which said microexplosive is housed, wherein said triggering rod comprises a rear end and a tapered forward end in contact with said initiating explosive on one side of said casing, wherein said receiving rod supports the other side of said casing, wherein said casing is positioned between said receiving rod and said triggering rod, wherein said apparatus further comprises means for striking said rear end of said triggering rod at a sufficiently high speed so as to trigger said initiating explosive.

16. The apparatus defined by claim 4 further comprising a liquid jet for directing a flow of liquid at the inner surface of said chamber to remove bubbles adhering to the inner surface of said chamber.

17. An apparatus in accordance with claim 1, wherein said container open mouth portion is positioned directly about said exterior side surface.

18. An apparatus for disintegrating a calculus in a human body, said apparatus comprising:
 (a) an entirely flexible container adapted to receive and hold a liquid, said container having a flexible open mouth portion;
 (b) a shock wave generation source positioned at least partially in said container, said shock wave generation source further being positioned within a substantially solid shock wave generation chamber having an interior surface solely in the form of an ellipsoid of revolution and a substantially solid exterior side surface, said flexible container further having an interior which is in fluidic communication with the interior surface of said shock wave generation chamber; and
 (c) means for attaching said exterior side surface of said shock wave generation chamber to an interior surface of the mouth of said container wherein most of the exterior side surface of said shock wave generation chamber is in fluidic communication with the interior of the flexible container.

19. The apparatus defined by claim 18, wherein said shock wave generation chamber is in communication with said container so that when said container is filled with liquid said shock wave generation chamber is filled with liquid, wherein said shock wave generation chamber interior surface is in the shape of a pseudo-ellipsoid of revolution having first and second foci, wherein said source is positioned substantially at said first focus, whereby the position of said second focus can be changed sufficiently to substantially coincide with the location of said calculus in response to said relative displacement of said source and said container while said container is in contact with said human body.

20. The apparatus defined by claim 18 wherein said source comprises means for generating a shock wave of sufficient strength at said first focus so as to disintegrate said calculus at said second focus.

21. The apparatus defined by claim 20 wherein said source comprises means for generating a shock wave at said first focus of sufficient strength to disintegrate a calculus at said second focus comprising a stone of calcium oxalate as large as 5 millimeters.

22. The apparatus defined by claim 21 wherein said human body is placed on a bed, wherein said apparatus further comprises means for displacing at least one of said bed and said chamber so as to position said calculus at said second focus.

23. The apparatus defined by claim 20 wherein said source comprises a microexplosive.

24. The apparatus defined by claim 20 wherein said source comprises a spark gap generating apparatus comprising a source of electricity and two spaced apart plates connected to said electricity source, wherein said source of electricity produces a spark in said gap at said first focus.

25. The apparatus defined by claim 20 wherein said source comprises a supersonic wave generation element.

26. The apparatus defined by claim 20 wherein said source comprises means for producing a laser beam, an optical fiber means, and a focusing lens, wherein one end of said optical fiber means is connected to said laser means and the other end of said optical fiber means is directed toward said lens, wherein said lens is so positioned to focus said laser beam outputted from said optical fiber means at substantially said second focus.

27. The apparatus defined by claim 20 further comprising a liquid jet directed toward the inner surface of said chamber for directing a flow of liquid at said inner surface of said chamber to remove bubbles adhering to said inner surface of said chamber.

28. The apparatus defined by claim 20 further comprising a pipe passing through said chamber so that one end of said pipe is positioned in said container, wherein the other end of said pipe is connected to a source of liquid, wherein said pipe comprises means for filling said container with said liquid.

29. The apparatus defined by claim 20 further comprising a pipe, and means for discharging liquid from said container through said pipe, wherein said pipe passes through said chamber so that one end of said pipe is positioned in said container, wherein the other end of said pipe is connected to said discharging means.

30. An apparatus in accordance with claim 18, wherein said exterior side surface is directly attached to the mouth of said container.

31. An apparatus for disintegrating a calculus in a human body, said apparatus comprising:
    (a) a shock wave generation chamber having a solely pseudo-elliptical interior surface, an end surface with an opening therethrough, and a substantially solid exterior side surface;
    (b) an entirely flexible container adapted to receive and hold a liquid, said container having an open mouth portion which is positioned about the exterior side surface of said shock wave generation chamber, said flexible container further having an interior which is in fluidic communication with the solely pseudo-elliptical interior surface and a portion of the exterior side surface of said shock wave generation chamber; and
    (c) means for attaching said exterior side surface of said shock wave generation chamber to an interior surface of the mouth of said container wherein most of the exterior side surface of said shock wave generation chamber is in fluidic communication with the interior of the flexible container.

32. The apparatus of claim 31 wherein said substantially solid exterior side surface of said shock wave generation chamber is substantially cylindrical.

33. An apparatus in accordance with claim 31, wherein said exterior side surface is directly attached to the mouth of said container.

* * * * *

UNITED STATES PATENT AND TRADEMARK OFFICE
CERTIFICATE OF CORRECTION

PATENT NO. : 4,893,614

DATED : January 16, 1990

INVENTOR(S) : K. TAKAYAMA et al.

It is certified that error appears in the above-identified patent and that said Letters Patent is hereby corrected as shown below:

```
     Column 2, line 12, delete "the" after "strong".
     Column 6, line 60, change "as" to ---is---.
     Column 6, line 63, change "a" to ---an--- after "in".
     Column  7,  line  27,  change  "explosive"  to  ---
microexplosive---.
     Column 3, line 12, insert ---27--- after "laser".
```

Signed and Sealed this

Sixth Day of August, 1991

Attest:

HARRY F. MANBECK, JR.

Attesting Officer

Commissioner of Patents and Trademarks